United States Patent
Rasche et al.

(10) Patent No.: US 6,574,493 B2
(45) Date of Patent: Jun. 3, 2003

(54) METHOD OF LOCALIZING OBJECTS IN INTERVENTIONAL RADIOLOGY

(75) Inventors: Volker Rasche, Hamburg (DE); Georg Schmitz, Roetgen (DE); Jörg Sabczynski, Norderstedt (DE); Waldemar Zylka, Hamburg (DE); Johannes Jacobus Van Vaals, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 78 days.

(21) Appl. No.: 09/792,097

(22) Filed: Feb. 23, 2001

(65) Prior Publication Data
US 2001/0034480 A1 Oct. 25, 2001

(30) Foreign Application Priority Data
Feb. 26, 2000 (DE) .......................... 100 09 166

(51) Int. Cl.⁷ ................................. A61B 5/05
(52) U.S. Cl. ..................................... 600/407
(58) Field of Search ............... 600/407, 408, 600/409, 410, 413, 419, 422, 423; 324/308, 309

(56) References Cited
U.S. PATENT DOCUMENTS

| | | | | |
|---|---|---|---|---|
| 5,235,510 A | * | 8/1993 | Yamada et al. ............ 600/300 |
| 5,769,789 A | * | 6/1998 | Wang et al. ............... 600/414 |
| 5,916,164 A | * | 6/1999 | Fitzpatrick et al. ......... 600/426 |
| 6,016,439 A | * | 1/2000 | Acker ...................... 600/411 |
| 6,121,775 A | * | 9/2000 | Pearlman .................. 324/309 |
| 6,275,721 B1 | * | 8/2001 | Darrow et al. ............ 600/410 |
| 6,419,680 B1 | * | 7/2002 | Cosman et al. ............ 606/130 |
| 6,434,413 B1 | * | 8/2002 | Liu et al. .................. 600/410 |
| 6,438,404 B1 | * | 8/2002 | Van Den Brink et al. .. 600/419 |
| 6,442,414 B1 | * | 8/2002 | Watanabe .................. 600/419 |
| 6,459,922 B1 | * | 10/2002 | Zhang ..................... 600/410 |
| 6,466,812 B1 | * | 10/2002 | Overweg et al. ........... 600/410 |
| 6,466,814 B1 | * | 10/2002 | Ardenkjaer-Larsen et al. ... 600/420 |

\* cited by examiner

Primary Examiner—Daniel Robinson
(74) Attorney, Agent, or Firm—John Vodopia

(57) ABSTRACT

The invention relates to a method enabling the localization of objects, for example surgical instruments, in interventional radiology. The method utilizes the known geometrical shape of the object to be localized in order to simulate projections therefrom for comparison with real projection images. Optimum correspondence between simulation and real image yields the desired object position and object orientation. The invention is based on digital image processing and can be used in conjunction with customary radiological diagnostic apparatus such as C-arm fluoroscopy apparatus, computed tomography apparatus or magnetic resonance tomography apparatus. Objects to be localized can be provided with markers whose spatial position yields an unambiguous projection image.

8 Claims, 2 Drawing Sheets

METHOD OF LOCALIZING OBJECTS IN INTERVENTIONAL RADIOLOGY

FIELD OF THE INVENTION

The invention relates to a method of localizing an object, notably in interventional radiology where a volume in which the object to be localized is present is examined by means of digital image processing on the basis of projection images. The invention also relates to a radiological diagnostic apparatus for carrying out the method, to surgical instruments used in interventional radiology, and to a computer program product that is used for digital image processing in interventional radiology.

BACKGROUND OF THE INVENTION

Generally speaking, the exact localization of given three-dimensional objects, for example catheters, needles, endoscopes, etc. is of crucial importance in interventional radiology. For example, in the case of X-ray guided biopsies a volume of possibly less than 1 mm$^3$ must be targeted by the puncture needle. In image-guided orthopedic surgery the positioning and orientation of, for example screws in the bone tissue must be monitored with a high degree of accuracy. For any type of minimum invasive intervention the surgeon must be capable of accurately determining the spatial position of the relevant instruments relative to the patient.

During a typical image guided intervention the patient is continuously monitored by means of X-rays. A C-arm X-ray apparatus which enables determination of the spatial position of a surgical instrument by carrying out X-ray fluoroscopy in two different, substantially perpendicular projection directions is preferably used for this purpose. The two images are simultaneously available to the surgeon, so that a three-dimensional impression can be obtained regarding the position and orientation of the surgical instrument in the region of surgery. For the monitoring of the surgery it is necessary to repeat the fluoroscopy of the patient at short time intervals so as to track the movement of the surgical instruments. Repeated change-overs may then occur he two projection directions of the C-arm fluoroscopy apparatus. The method is complex and time-consuming and, moreover, implies an excessive exposure to ionizing radiation both for the patient as well as the surgeon.

U.S. Pat. No. 5,772,594 proposes a system for image-guided surgery where the patient, the X-ray apparatus and the part of a surgical instrument that is situated outside the patient are provided with light-emitting diodes (LEDs). The relative spatial position of the patient, the X-ray apparatus and surgical instrument is determined by means of an optical measuring system. The position of the surgical instrument can be correlated to the X-ray images by means of X-ray opaque markers which are also provided on the patient. A digital image processing system serves to superpose an image of the position and the orientation of the surgical instrument on the various X-ray images.

Such a known optically operating system for image-guided surgery has a drawback in that it requires a large amount of additional hardware. The application is limited to surgical apparatus suitably provided with light-emitting diodes which can thus be localized by the image processing system. It is a further drawback that motions of the patient must be excluded during the procedure, as otherwise the spatial position of the surgical instrument can no longer be correctly correlated to the X-ray images.

Therefore, it is an object of the present invention to provide a method of localizing an object which does not require additional apparatus components and enables reliable, continuous and fully automatic determination of the position and the orientation of an object, notably a surgical instrument. The spatial position of an object relative to the patient should thus be visualized in the case of the application in interventional radiology.

This object is achieved by a method of the kind set forth in that projections of the object to be localized, whose geometrical shape is known, are simulated and compared with the projection image of the volume examined.

SUMMARY OF THE INVENTION

The method according to the invention utilizes two-dimensional projection images as they are formed, for example by means of X-ray fluoroscopy, in order to derive therefrom the position and orientation of the object. The digital image processing of the two-dimensional data set imposes comparatively easy requirements as regards the capability of the data processing system used. Therefore, the method according to the invention can be implemented in practically any standard computer system used for image processing in radiological diagnostic apparatus. Thus, exclusively a pure software extension in existing radiological diagnostic apparatus is involved; such an extension can be realized at all times and at low costs.

Most applications in interventional radiology involve the localization of objects whose geometrical shape is known. When a three-dimensional geometrical model, for example a surgical instrument, is presented to the digital image processing, two-dimensional projection images can be calculated therefrom. This simulation is to be based not only on the geometrical object data but also on a respective, apparatus-specific model of the image formation (camera model). Comparison of the calculated projections and the real projection image then simply enables determination of the desired object position and orientation.

The method according to the invention requires in principle only a single two-dimensional image for object localization. This obviates in principle the necessity of changing over between different projection directions for three-dimensional object localization. The three-dimensional information is available at all times, because the processing of the comparatively small amount of data of the two-dimensional image data set can be performed within a very short period of time.

However, the reliability and the accuracy of the method can be enhanced substantially by using a plurality of real projection images with each time different projection directions, if possible, for the localization. The use of two or more projection images is advantageous notably when the two-dimensional projection of the object to be localized does not provide unambiguous information as regards the exact position and orientation.

The simulation of the projections is performed on the basis of the six object degrees of freedom (position and orientation). Because of the small number of parameters taken into account in the simulation, the localization method according to the invention is extremely fast with easy requirements imposed on the computer hardware, very robust and easy to implement.

The object localization is preferably carried out in such a manner that the simulation is iteratively repeated while systematically varying the degrees of freedom of the object until the deviations between calculated simulation and real projection image become minimum. The procedure can be interrupted as soon as the object position and the object orientation have been determined with the predetermined accuracy. The correspondence between the simulated projection and the real image is evaluated by means of image processing and recognition algorithms that are known per se.

The method according to the invention can be advantageously simplified further by providing the object to be localized with one or more markers which are reproduced in the projection image. The markers may have a very simple geometrical shape that can be presented to the image processing system with a minimum expenditure. The simulation of the projections of such markers is even substantially simpler than the calculation of possibly complex three-dimensional objects. The localization method can thus be carried out even faster and more effectively. The determination of the desired object position and object orientation is then performed on the basis of the knowledge of the arrangement of the markers relative to the object to be localized.

Because the localization method according to the invention utilizes a two-dimensional projection image for determining the object position, said markers should be configured in such a manner that their projection image offers unambiguous information as regards the exact position and the orientation. Particularly suitable in this respect are markers that consist of line-like, intersecting structures, the line segments being subdivided into lengths with each time a different length ratio by the point of intersection. Because of the magnitude and the position of the projection image of the marker, the object position can be unambiguously determined; as a result of the different length ratios of the marker segments, a projection image is unambiguously associated with any arbitrary object orientation.

For the determination of the spatial position and orientation of an object by means of the method according to the invention it is advantageous to use a three-dimensional volume model that is acquired by means of three-dimensional magnetic resonance or computed tomography. In the clinical field in which the method according to the invention is used, three-dimensional volume images can usually also be acquired by means of said methods. The geometrical data of objects to be localized which is thus acquired, be it surgical instruments or also bones or internal organs of a patient, can then be used as basis for the simulation of projection images according to the invention. In that case the objects to be localized can again be provided with the above-mentioned markers. The volume data can then be used to determine the arrangement of the markers on the object to be localized.

The localization method according to the invention can be carried out by means of a radiological diagnostic apparatus provided with a patient table, a digital imaging system, a computer and at least one display device, an apparatus-specific, mathematical model of the imaging, geometrical data of objects to be localized and a localization program being stored in the working memory of the computer, the parameters concerning object position and object orientation relative to the patient table being determined on the basis of the apparatus data and object data from the projection image so as to be visualized on the display device.

Radiological diagnostic apparatus provided with the described hardware find standard use in interventional radiology. The localization method according to the invention is implemented in the computer used for the image processing. This requires an apparatus-specific camera model, so that projection images can be calculated on the basis of the geometrical data of the objects to be localized. The object position and the object orientation relative to the patient table are then determined from the correspondence between the simulated projections and the real projection image, so that the complete information concerning the object position relative to the patient is available. On the basis of the parameters concerning object position and object orientation determined, the three-dimensional position of the object can be reproduced on the display device; it is possible, for example, to superpose the localized object in different views on real projection images of the volume examined.

As has already been stated, notably C-arm fluoroscopy apparatus are widely used in interventional radiology. In such apparatus the patient is irradiated by a cone-shaped X-ray beam which emanates from an X-ray source which is arranged so as to face a fluoroscopic imaging system. The digital projection images thus produced can be used directly for the localization method according to the invention. The camera model required for this purpose contains information as regards the distance between the X-ray source and the imaging system (detector) as well as information concerning the point of intersection of the optical axis and the detection plane. These parameters define inter alia the magnification factor during the exposure. This factor, of course, must be taken into account for the three-dimensional localization.

The method according to the invention, however, can also be readily used for computed tomography apparatus or magnetic resonance tomography apparatus. Computed tomography apparatus customarily produce either slice images or three-dimensional volume images. Therefore, such apparatus may require an additional data processing step to form the necessary projection images therefrom. In the case of magnetic resonance tomography apparatus it is in principle possible to dispense with the slice selection during the image acquisition or to select comparatively thick slices by means of a suitable combination of magnetic field gradients and corresponding RF pulses. Instead of the customary slice images, projection images of a predetermined volume can thus be acquired directly in projection directions that can be freely selected. Such projection images can then be used for the object localization in conformity with the invention.

Increasing use is made of interventional radiology in computed tomography or magnetic resonance tomography apparatus. Such systems always include a high-performance computer system for image processing. In such systems the localization method based on projection images according to the invention is particularly suitable for carrying out a fast and reliable object localization with a possibility for incorporating the localized object in the various visualization facilities provided in such systems.

Surgical instruments that are suitable for use in interventional radiology in conjunction with the localization method according to the invention have at least one marker which is geometrically shaped in such a manner that its two-dimensional projection image can be unambiguously associated with the position and the orientation of the marker. It is particularly advantageous to use a marker which consists of line-like, intersecting structures which are subdivided into segments with different respective length ratios at their point of intersection.

As has already been described, markers of this kind have advantageous properties with a view to the determination of the position and the orientation of the surgical instrument from projection images. When imaging is performed by means of X-ray fluoroscopy or computed tomography, the markers are preferably X-ray opaque or X-ray semi-transparent. Granted, X-ray opaque markers produce a very distinct contrast in the projection image which is very advantageous for digital image processing. However, semi-transparent markers offers the advantage that they are not masked by any image elements that could cause the loss of important information for the surgeon in given circumstances. Semi-transparent markers also offer the advantage that they can be removed from the images at a later stage by means of known image processing techniques. A suitable compromise which takes into account the advantages of semi-transparent markers and the requirements imposed on object localization to the same extent is obtained when the markers consist of a combination of X-ray opaque and X-ray semi-transparent elements.

Surgical instruments used for interventional radiology in magnetic resonance tomography apparatus preferably are provided with markers consisting of a magnetic resonance contrast substance.

It may be advantageous to provide further objects with the described markers. Eligible in this respect are parts of the radiological diagnostic apparatus used, for example the patient table, but also the patient him or herself qualify. Bones, internal organs, implants etc. can be provided with markers so that their spatial position can be determined at all times by means of the localization method according to the invention. The surgeon thus has the possibility of exactly determining the relative spatial arrangement of the instruments used relative to the patient, at all times, without it being necessary to revert to pre-operatively formed volume images of the patient.

As described above, the method according to the invention can be advantageously used in conjunction with normal, computer-aided radiological diagnostic apparatus, because it is merely necessary to provide a computer program for the digital image processing; such a program calculates two-dimensional projection images from the geometrical data of an object while taking into account a camera model and compares the projection images with the radiologically acquired image data.

BRIEF DESCRIPTION OF THE DRAWINGS

Embodiments of the invention will be described in detail hereinafter with reference to the drawing. Therein.

DETAILED DESCRIPTION OF THE PREFERRED EMBODIMENTS

Figure 1:
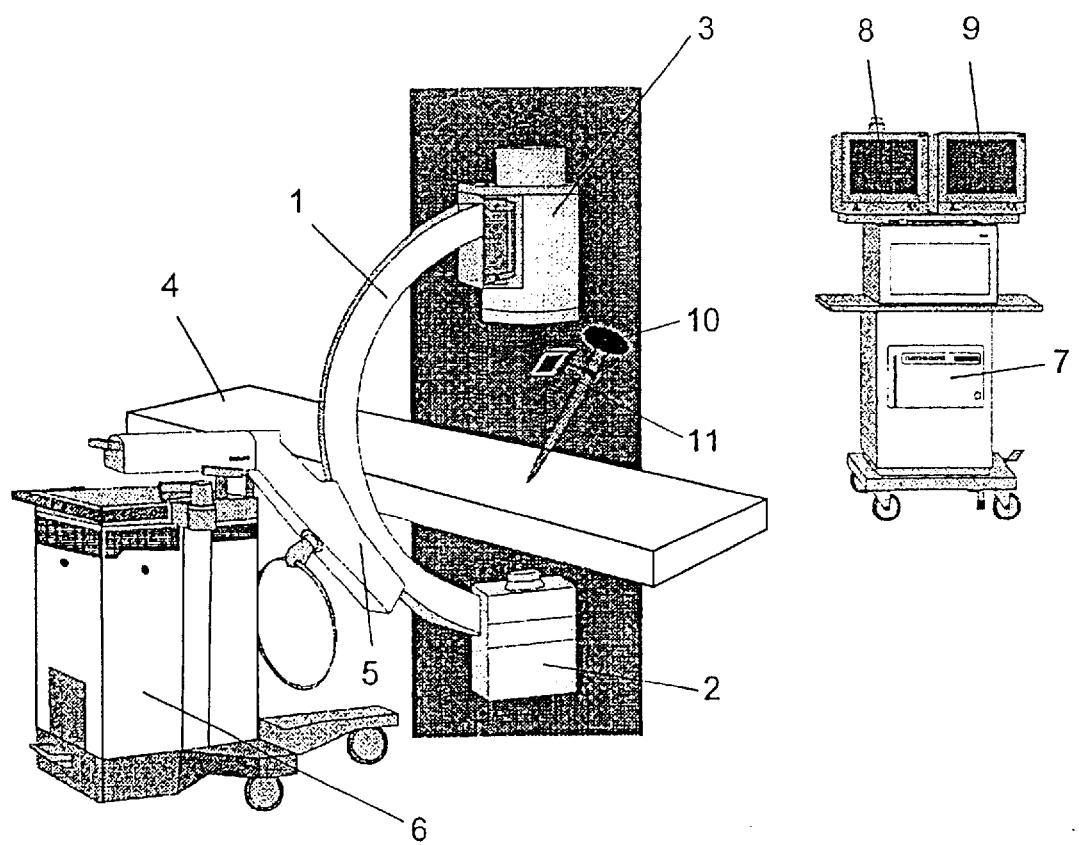
FIG. 1 shows a C-arm fluoroscopy apparatus for use according to the invention.

FIG. 1 shows a C-arm X-ray apparatus as customarily used in interventional radiology. An X-ray source 2 and a facing fluoroscopic imaging system 3 are mounted on the C-arm 1. The patient is accommodated on a patient table 4 and is irradiated by a conical X-ray beam. The C-arm 1 is journaled so as to be pivotable in a guide 5 so that the fluoroscopy direction can be rotated about an axis extending parallel to the patient table 4. The C-arm is mounted on a displaceable carriage 6 which at the same time accommodates control and power supply components of the X-ray system. The X-ray fluoroscopy apparatus communicates with an image processing and visualization system which consists of a computer 7 for digital image processing and two monitors 8 and 9 for graphic reproduction and display of the X-ray projections. Also shown is a surgical instrument 10 which is present in the irradiated volume above the patient table 4. The position as well as the orientation of the instrument 10 can be determined by means of the method according to the invention while utilizing a marker 11 which is also reproduced as a projection during fluoroscopy. The marker 11 is rigidly connected to the surgical instrument 10. The spatial position of the surgical instrument 10, whose geometrical shape is known, can be determined on the basis of the projection image of the marker 11; this position can be displayed on the monitors 8 and 9 in different views in such a manner that the surgeon is given, for example, while performing a surgical intervention, a three-dimensional impression of the situation of the surgical instrument 10 relative to the patient accommodated on the patient table 4.

Figure 2:
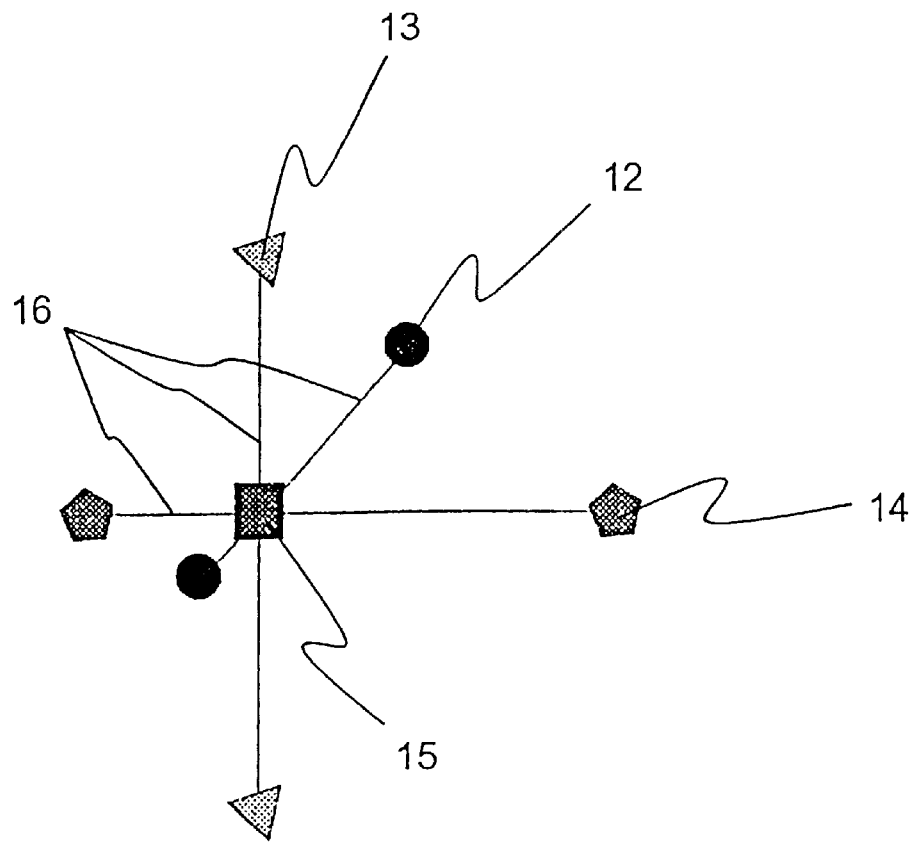
FIG. 2 shows (diagrammatically) markers according to the invention.

FIG. 2 shows a marker which, in conformity with the method according to the invention, is suitable to determine the position and the orientation of an object from a projection image. The marker consists of marker elements 12, 13, 14, 15 which can be distinguished on the basis of their geometrical shape. Two oppositely situated markers of the same shape define respective connecting axes 16. These connecting axes intersect in a common point of intersection denoted by the marker element 15. The three connecting axes 16 are subdivided into segments with different length ratios by the common point of intersection 15. In the embodiment shown, the connecting axis associated with the marker elements 12 is subdivided approximately with a ratio of 1:3, the connecting axis associated with the marker elements 13 approximately with the ratio 1:1 and the connecting axis associated with the marker elements 14 approximately with the ratio 1:2. The three connecting axes are arranged so as to be orthogonal to one another. In conformity with the method according to the invention, the object position and orientation can be unambiguously determined from the projection image of the marker shown.

Figure 3:
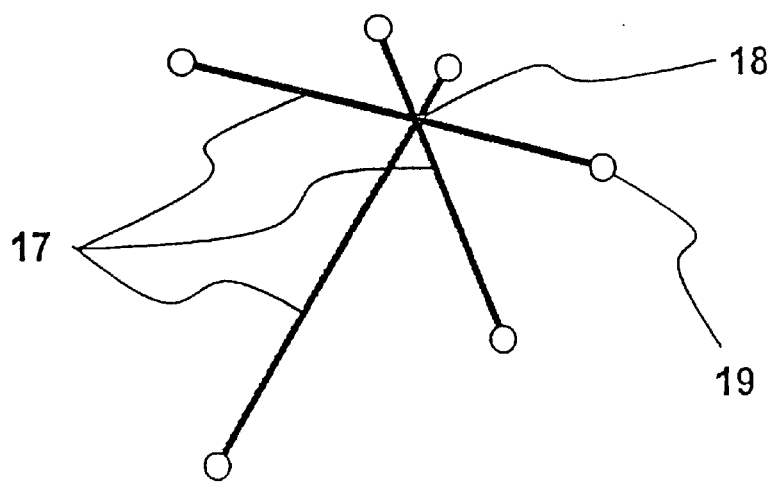
FIG. 3 shows semi-transparent markers in combination with X-ray opaque elements.

FIG. 3 shows a marker consisting of three orthogonally arranged line-like elements 17. These elements are made of an X-ray semi-transparent material so that as little as possible image information of the volume examined is lost due to the marker. The three line-like elements 17 are again subdivided into segments with different length ratios by their common point of intersection 18. The localization in conformity with the method according to the invention is more reliable and more effective when the marker lines 17 are additionally provided with X-ray opaque elements 19 at their ends.

What is claimed is:

1. A method of localizing a surgical instrument, notably in interventional radiology where a volume in which the surgical instrument to be localized is present is examined by means of digital image processing on the basis of a plurality of projection images, where the geometrical shape of the surgical instrument is known, comprising the steps of simulating and comparing at least one projection image of the surgical instrument to be localized with the projection image of the volume examined, wherein the surgical instrument to be localized is provided with at least one marker which is reproduced in the at least one projection image.

2. A method as claimed in claim 1, wherein the simulation is repeated, while systematically varying the parameters concerning position and orientation of the surgical instrument, until optimum correspondence with the projection image is achieved.

3. A method as claimed in claim 1, wherein the marker is geometrically shaped in such a manner that the position and the orientation of the marker can be unambiguously correlated with its two-dimensional projection image.

4. A method as claimed in claim 1, wherein the marker consists of line-like, intersecting structures which are subdivided into segments with different respective length ratios at their point of intersection.

5. A method as claimed in claim 1, wherein a volume model of the surgical instrument to be localized is used for the simulation of the projections, said volume model being acquired by means of three-dimensional magnetic resonance tomography or computed tomography.

6. A method as claimed in claim 1, wherein the method is performed by a radiological diagnostic apparatus which includes a patient table, a digital imaging system, a computer and at least one display device, and wherein an apparatus-specific, mathematical model of the imaging, geometrical data of objects to be localized and a localization program are stored in the working memory of the computer, said program determines the parameters concerning position and orientation of the surgical instrument relative to the patient table on the basis of the apparatus data and the surgical instrument data from the projection image so as to be visualized on the display device.

7. A method as claimed in claim 6, wherein the radiological diagnostic apparatus is selected from the group consisting of an X-ray fluoroscopy apparatus, a computed tomography apparatus, and a magnetic resonance tomography apparatus.

8. A method of localizing an object, notably in interventional radiology where a volume in which the object to be localized is present is examined by means of digital image processing on the basis of a plurality of projection images, where the geometrical shape of the object is known, comprising the steps of simulating and comparing at least one projection image of the object to be localized with the projection image of the volume examined, wherein the object to be localized is provided with at least one marker which is reproduced in the at least one projection image, and wherein the marker consists of line-like, intersecting structures which are subdivided into segments with different respective length ratios at their point of intersection.

* * * * *